US009550813B2

(12) United States Patent
Lu et al.

(10) Patent No.: US 9,550,813 B2
(45) Date of Patent: Jan. 24, 2017

(54) DISULFIDE STABILIZED FOLDON POLYPEPTIDES

(71) Applicant: The Board of Trustees of the Leland Stanford Junior University, Palo Alto, CA (US)

(72) Inventors: Yuan Lu, Palo Alto, CA (US); James R. Swartz, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/401,754

(22) PCT Filed: May 22, 2013

(86) PCT No.: PCT/US2013/042229
§ 371 (c)(1),
(2) Date: Nov. 17, 2014

(87) PCT Pub. No.: WO2013/177283
PCT Pub. Date: Nov. 28, 2013

(65) Prior Publication Data

US 2015/0141616 A1 May 21, 2015

Related U.S. Application Data

(60) Provisional application No. 61/650,337, filed on May 22, 2012.

(51) Int. Cl.
*C07K 14/005* (2006.01)
*C12P 21/02* (2006.01)
*C12N 7/00* (2006.01)

(52) U.S. Cl.
CPC ............... *C07K 14/005* (2013.01); *C12N 7/00* (2013.01); *C12P 21/02* (2013.01); *C07K 2319/22* (2013.01); *C07K 2319/35* (2013.01); *C07K 2319/40* (2013.01); *C07K 2319/42* (2013.01); *C07K 2319/50* (2013.01); *C07K 2319/735* (2013.01); *C12N 2760/16022* (2013.01); *C12N 2760/16034* (2013.01); *C12N 2795/10122* (2013.01)

(58) Field of Classification Search
None
See application file for complete search history.

(56) References Cited

U.S. PATENT DOCUMENTS

| | | | |
|---|---|---|---|
| 2005/0003548 A1 | 1/2005 | Korokhov et al. |
| 2010/0168402 A1 | 7/2010 | Bundy et al. |
| 2010/0297174 A1 | 11/2010 | Garcia-Sastre et al. |
| 2011/0020378 A1 | 1/2011 | Burkhard |

*Primary Examiner* — Lianko Garyu
(74) *Attorney, Agent, or Firm* — Pamela J. Sherwood; Bozicevic, Field & Francis LLP

(57) ABSTRACT

Intermolecular disulfide stabilized foldon polypeptides are provided.

10 Claims, 8 Drawing Sheets

Trimeric foldon

H-bond topology of the trimeric foldon β-hairpin propeller

The starting antigen concentrations were the same 6 μg/ml.

DISULFIDE STABILIZED FOLDON POLYPEPTIDES

GOVERNMENT RIGHTS

This invention was made with Government support under contract AI057229 awarded by the National Institutes of Health. The Government has certain rights in the invention.

BACKGROUND OF THE INVENTION

The C-terminal domain of T4 fibritin (foldon) is obligatory for the formation of the fibritin trimer structure and has been used as an artificial trimerization domain. Its native structure consists of a trimeric β-hairpin propeller. Foldon trimerization is one of the fastest bimolecular protein associations reported in the literature.

At low pH, the foldon trimer disintegrates into a monomeric (A-state) form that has similar properties as that of an early intermediate of the trimer folding pathway. The formation of this A-state monomer from the trimer, its structure, thermodynamic stability, equilibrium association and folding dynamics have been characterized to atomic detail by modern high-resolution NMR techniques. The foldon A-state monomer forms a β-hairpin with intact and stable H-bonds that is similar to the monomer in the foldon trimer, but lacks a defined structure in its N and C-terminal parts. Suggested mechanisms for the action of the foldon imply that, as an autonomous folding domain, it is the first to trimerize, providing a "template" that brings the sequences into close proximity and correct register. By acting as a kinetic seed, the foldon can drive the correct pairing of fused domains and tether the terminal ends of the nascent structure together The ability to trimerize proteins is of great interest for biomaterials and nanotechnology applications. The foldon domain is a versatile trimerization motif and can be combined with a variety of proteins. Further optimization of the domain for specific purposes is defined herein.

RELEVANT LITERATURE

Publications relating to the use of foldon in the construction of influenza vaccines include, inter alia, US 2009/0208531.

Methods of introducing unnatural amino acids during CFPS are described in patent publication US 2010-0093024 A1. Methods of directly linking antigens and other polypeptides to a virus-like particle through unnatural amino acids are described in patent application US-2010-0168402-A1. Methods of encapsidating virus-like particles produced by CFPS are described in patent publication US-2010-0167981-A1. Each of these documents are herein specifically incorporated by reference.

SUMMARY OF THE INVENTION

Foldon polypeptides are provided, in which two amino acids of the native sequence are substituted with cysteine residues that provide for intermolecular disulfide bonding. The trimeric foldon protein is thus stabilized and is maintained as a trimer under conditions otherwise unfavorable to retention of the quaternary structure. The foldon polypeptides of the invention find particular use as a component of a fusion protein, for any purpose where it is desirable to have a stable trimeric structure. Non-limiting examples of fusion proteins are bacterial, viral, mammalian, pathogen, etc. proteins of interest fused to a foldon of the invention, where the protein of interest may include influenza hemagglutinin, for example the HA stem or head, collagen, gp26, etc. The foldon domain may be C-terminal to the fusion partner, or may be N-terminal to the fusion partner. In some embodiments the foldon domain is present at the C-terminus of the fusion protein. In some embodiments a tag for purification is additionally fused to the foldon domain, e.g. at the C-terminus. In some embodiments an unnatural amino acid is introduced into the fusion protein, e.g. at a site C-terminal to the foldon domain. In some embodiments the unnatural amino acid is used to link the trimeric protein to a virus like particle (VLP). In some embodiments a flexible linker is used to link the foldon domain and the protein of interest, for example a linker of up to 5, 8, 10, 12, 15, 18, 20, 21, 25 amino acids in length.

The foldon polypeptides of this invention can be made by transforming host cells with nucleic acid encoding the polypeptide, culturing the host cell and recovering the polypeptide from the culture, or alternatively by generating a nucleic acid construct encoding the foldon polypeptides and producing the polypeptide by cell free synthesis, which synthesis may include coupled transcription and translation reactions. Also provided are vectors and polynucleotides encoding the foldon polypeptides.

In one embodiment of the invention, a method is provided for the cell-free protein synthesis (CFPS) of the fusion protein of the invention. In some embodiments the CFPS product is isolated from the reaction mixture and refolded prior to formulation. In some embodiments the refolding is performed in the presence of a detergent, usually a nonionic detergent. The detergent may be present at a concentration of from about 0.01 to 0.1%, usually around 0.05%. Detergents of interest include nonionic polyoxyethylene surfactants, e.g. Brij 35; Tween 20, etc.

DETAILED DESCRIPTION OF THE EMBODIMENTS

Figure 1:
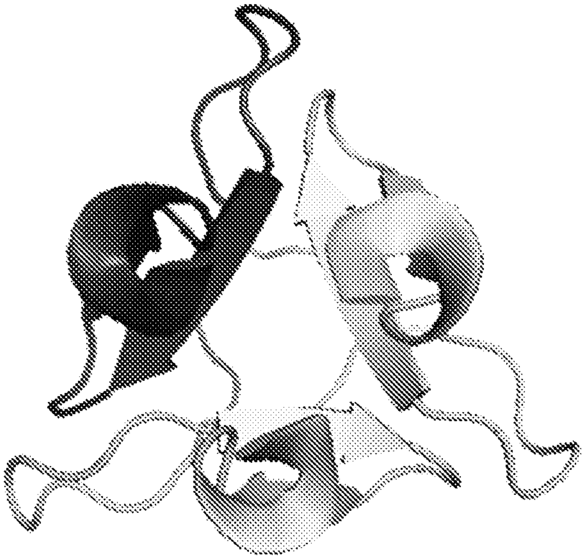
FIG. 1 Structure of trimeric foldon.
Figure 1:
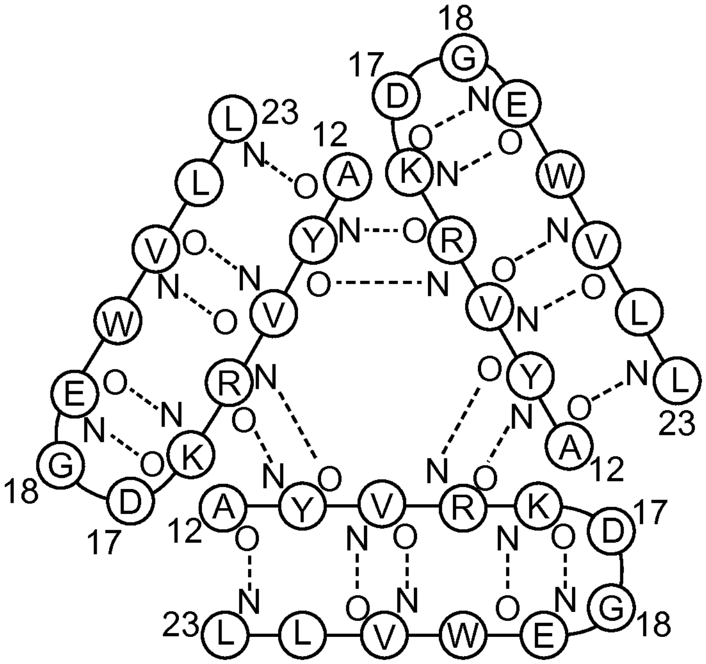

Foldon polypeptides are provided in which the quaternary trimer structure is stabilized by intermolecular disulfide bonds. The trimeric foldon protein is thus stabilized and is maintained as a trimer under conditions otherwise unfavorable to retention of the quaternary structure. The foldon polypeptides of the invention find particular use as a component of a fusion protein, for any purpose where it is desirable to have a stable trimeric structure. In some embodiments an unnatural amino acid is introduced into the fusion protein, e.g. at a site C-terminal or N-terminal to the foldon domain. In some embodiments the unnatural amino acid is used to link the trimeric protein to a virus like particle (VLP).

In some embodiments, the invention provides a use of a conjugate, compound, or composition herein in the manufacture of a medicament. In an embodiment, the invention provides a use of a conjugate, compound, or composition herein in the manufacture of a medicament, e.g. a vaccine, for the prevention or treatment of an infection. In some embodiments, the invention provides a use of a conjugate, compound, or composition herein for the prevention or treatment of an infection.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "foldon" or "foldon domain" refers to the C-terminal amino acid peptide sequence of the bacteriophage T4 fibritin sequence or portions thereof, or fragments thereof having foldon activity. Foldon is capable of forming a trimeric structure. Foldon activity refers to the ability of foldon to form trimers. In one aspect, foldon refers to the native amino acid sequence of SEQ ID NO:1, GYIPEAPRDGQAYVRKDGEWVLLSTF or any fragments or variants thereof having foldon activity. Of particular interest are the cysteine stabilized amino acid variants set forth in Table 1. Foldon adopts a β-propeller conformation, and can fold and trimerize in an autonomous way.

As used herein, the terms "purified" and "isolated" when used in the context of a polypeptide that is substantially free of contaminating materials from the material from which it was obtained, e.g. cellular materials, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide that is chemically synthesized refers to a polypeptide which is substantially free of chemical precursors or other chemicals which are involved in the syntheses of the polypeptide. In some embodiments, an influenza hemagglutinin stem domain polypeptide of the invention is produced by cell-free protein synthesis. In other specific embodiments, an influenza hemagglutinin stem domain polypeptide of the invention is produced by recombinant methods in a cell.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

An "effective amount" or a "sufficient amount" of a substance is that amount sufficient to cause a desired biological effect, such as beneficial results, including clinical results, and, as such, an "effective amount" depends upon the context in which it is being applied. In the context of this invention, an example of an effective amount of a vaccine is an amount sufficient to induce an immune response (e.g., antibody production) in an individual. An effective amount can be administered in one or more administrations.

Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein may be important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

Separation procedures of interest include affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Preferably a microsphere or matrix is used as the support for affinity chromatography. Such supports are known in the art and are commercially available, and include activated supports that can be combined to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

Proteins may also be separated by ion exchange chromatography, and/or concentrated, filtered, dialyzed, etc., using methods known in the art. The methods of the present invention provide for proteins containing unnatural amino acids that have biological activity comparable to the native protein. One may determine the specific activity of a protein in a composition by determining the level of activity in a functional assay, quantitating the amount of protein present in a non-functional assay, e.g. immunostaining, ELISA, quantitation on coomasie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater.

By "fused" or "operably linked" herein is meant that two or more polypeptides are linked together to form a continuous polypeptide chain. As outlined in the Examples, the fusion polypeptide (or fusion polynucleotide encoding the fusion polypeptide) can comprise further components as well, including multiple peptides at multiple loops, fusion partners, etc. The precise site at which the fusion is made is not critical; particular sites are well known and may be selected in order to optimize the biological activity, secretion or binding characteristics of the binding partner. The optimal site will be determined by routine experimentation.

The terms "fusion partner protein" or "selected protein" are used interchangeably and refer generally to any peptide or protein of interest, usually having more than about 10, 15, 20, 30, 40, 50 or more amino acids that is fused to a foldon domain of the invention. In some embodiments the fusion partner is a structural protein, e.g. a collagen, keratin, actin, myosin, elastin, fibrillin, lamin, etc. In some embodiments the fusion partner is an immunogen, e.g. a pathogen protein useful in immunization, including without limitation influenza proteins such as hemagglutinin. Virus coat proteins of interest include any of the known virus types, e.g. dsDNA viruses, such as smallpox (variola); vaccinia; herpesviruses including varicella-zoster; HSV1, HSV2, KSVH, CMV, EBV; adenovirus; hepatitis B virus; SV40; T even phages such as T4 phage, T2 phage; lambda phage; etc. Single stranded DNA viruses include phiX-174; adeno-associated virus, etc. Negative-stranded RNA viruses include measles virus; mumps virus; respiratory syncytial virus (RSV); parainfluenza viruses (PIV); metapneumovirus; rabies virus; Ebola virus; influenza virus; etc. Positive-stranded RNA viruses include polioviruses; rhinoviruses; coronaviruses; rubella; yellow fever virus; West Nile virus; dengue fever viruses; equine encephalitis viruses; hepatitis A and hepatitis C viruses; tobacco mosaic virus (TMV); etc. Double-stranded RNA viruses include reovirus; etc. Retroviruses include rous sarcoma virus; lentivirus such as HIV-1 and HIV-2; etc.

Examples of polypeptides suitable as fusion partners include, but are not limited to, antigenic proteins such as tumor antigens, viral proteins, bacterial proteins, including tuberculosis antigens, protozoan proteins, including malarial proteins, renin; growth hormones, including human growth hormone; bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies particularly single chain Fv antibodies; and fragments of any of the above-listed polypeptides.

Virus Like Particle.

As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. In the methods of the invention, the cell-free synthesis reaction mixture provides conditions permissive for self-assembly into the capsid structure, even where the concentration of coat proteins may be dilute relative to the concentrations associated with in vivo viral synthesis.

A stable VLP maintains the association of proteins in a capsid structure under physiological conditions for extended periods of time, e.g. for at least about 24 hrs, at least about 1 week, at least about 1 month, or more. A feature of the stabilized foldon domains of the invention is the ability to maintain a trimeric quarternary structure under such conditions, thereby maintaining the association of all chains in a trimer for extended periods of time. Once assembled, the foldon linked VLP can have a stability commensurate with the native virus particle, e.g. upon exposure to pH changes, heat, freezing, ionic changes, etc. In some embodiments there is sufficient antigen in a foldon fusion protein and/or adjuvant molecules on the surface of the VLP so that when a VLP preparation is formulated into an immunogenic composition and administered to an animal or human, an immune response (cell-mediated or humoral) is raised.

Unnatural Amino Acids.

Examples of unnatural amino acids that can be used in the methods of the invention include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynyl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline, etc.

Unnatural amino acids of interest include, without limitation, amino acids that provide a reactant group for CLICK chemistry reactions (see *Click Chemistry: Diverse Chemical Function from a Few Good Reactions*, Hartmuth C. Kolb, M. G. Finn, K. Barry Sharpless, Angewandte Chemie International Edition, Volume 40, 2001, P. 2004, herein specifically incorporated by reference). For example, the amino acids p-acetyl-L-phenylalanine, p-propargyloxyphenylalanine, and p-azido-L-phenylalanine are of interest.

Linker.

The foldon domain and fusion partner may be joined through a linker, for example where the three-dimensional structure of the fusion partner does not permit a stabilized trimer structure without a linker. The linker length may be determined empirically or by calculation of steric distances. If used, the linker peptide should be of a type (length, amino acid composition, amino acid sequence, etc.) that is adequate to link the fusion partners in such a way that they assume a conformation relative to one another such that the resulting multimeric polypeptide has the desired activity.

The linker peptide may predominantly include the amino acid residues Gly, Ser, Ala and/or Thr. The linker typically comprises 1-25 amino acid residues, such as a sequence of about 2-20 or 3-15 amino acid residues. Likewise, the amino acid residues selected for inclusion in the linker peptide should exhibit properties that do not interfere significantly with the activity of the multimeric polypeptide. Thus, the linker peptide should on the whole not exhibit a charge which would be inconsistent with the desired activity of the multimeric polypeptide, or interfere with internal folding, or form bonds or other interactions with amino acid residues in one or more of the monomers which would seriously impede the binding of the multimeric polypeptide to the ligand-binding domain of the receptor. Specific linkers for use in the present invention may be designed on the basis of known naturally occurring as well as artificial polypeptide linkers. For instance, linkers such as a 15mer consisting of three repeats of a SEQ ID NO: 12 Gly-Gly-Gly-Gly-Ser amino acid sequence ($(Gly_4Ser)_3$), may be useful. Other non-limiting examples of linkers that are useful in the present invention are (e.g., $(GS)_n$, $(G_4S)_n$, $(GSA)_n$, SEQ ID NO:13 $A(EAAAK)_nA$, $(AP)_n$. Furthermore, phage display technology as well as selective infective phage technology can be used to diversify and select appropriate linker sequences.

Polypeptides

Foldon polypeptides are provided in which the quaternary trimer structure is stabilized by the introduction of cysteine residues that form intermolecular disulfide bonds. Polypeptides of the invention comprise the sequence of SEQ ID NO:1, wherein two amino acids are substituted with cysteine. In some embodiments the amino acid substitutions are selected from [G10C, D17C]; [R8C, D17C]; [R8C, G18C]; [P7C, G18C]; [A12C, K16C]; and [Y13C, R15C]. The respective amino acid sequences are set forth in SEQ ID NO:2, 3, 4, 5, 6 and 7, as set forth in Table 1 below. In some embodiments the stabilized foldon polypeptide comprises the amino acid sequence of SEQ ID NO:2, 3, 4 or 6.

The selection of a variant for use with a fusion partner of interest may be performed through routine testing, for example by fusing to the foldon candidates to the partner of interest, and analyzing the resulting polypeptides for the presence of cysteine stabilized trimer structure, to determine which of SEQ ID NO:2, 3, 4, 5, 6 or 7 provides for the desired stabilized structure, i.e. disulfide bond formation.

TABLE 1

| | amino acid sequence |
|---|---|
| Native<br>SEQ ID NO: 1 | GYIPEAPRDGQAYVRKDGEWVLLSTFL |
| A: G10-D17<br>SEQ ID NO: 2 | GYIPEAPRDCQAYVRKCGEWVLLSTFL |
| B: R8-D17<br>SEQ ID NO: 3 | GYIPEAPCDGQAYVRKCGEWVLLSTFL |
| C: R8-G18<br>SEQ ID NO: 4 | GYIPEAPCDGQAYVRKDCEWVLLSTFL |
| D: P7-G18<br>SEQ ID NO: 5 | GYIPEACRDGQAYVRKDCEWVLLSTFL |
| E: A12-K16<br>SEQ ID NO: 6 | GYIPEAPRDGQCYVRCDGEWVLLSTFL |
| F: Y13-R15<br>SEQ ID NO: 7 | GYIPEAPRDGQACVCKDGEWVLLSTFL |

In some embodiments of the invention, a monomeric form of the cysteine-containing foldon polypeptide is provided. In other embodiments a trimeric form of the cysteine-containing foldon polypeptide is provided. In some embodiments the trimeric structure is stabilized by intermolecular disulfide bonds.

The polypeptides of the invention may be synthesized, particularly in prokaryotic systems (which include CFPS reactions) as insoluble inclusion bodies. Such proteins may be washed, denatured, e.g. in the presence of 8 M urea, purified and refolded. While those of skill in the art are familiar with protein refolding processes, one refolding buffer useful in the present invention may comprise a cystamine/cysteamine redox buffer system and may comprise a nonionic surfactant.

If desired, various groups may be introduced into the peptide during synthesis or during expression, which allow for linking to other molecules or to a surface. The introduced groups need not be included in the foldon domain itself, but may be introduced as a tag or fusion C-terminal or N-terminal to the foldon domain. Thus cysteines can be used to make thioethers, histidines for linking to a metal ion complex, carboxyl groups for forming amides or esters, amino groups for forming amides, and the like. In some embodiments an unnatural amino acid is included at one or more defined sites in the protein, including without limitation, C-terminal to the foldon domain.

The foldon polypeptides of the invention may include an unnatural amino acid for the control of direct protein attachment, e.g. to virus like particles. Virus structural proteins that have been modified to comprise an unnatural amino acid and have assembled into a carrier VLP can be reacted with a foldon polypeptide, usually a foldon fusion polypeptide that also comprises an unnatural amino acid. The unnatural amino acid on the virus structural protein, or "carrier", is different from, and reactive with, the unnatural amino acid present on the foldon polypeptide(s).

Where the unnatural amino acids comprise reactive azide and alkyne groups, the reaction between foldon and carrier may by catalyzed with a copper(I) catalyst at a concentration sufficient for catalysis, e.g. at least about 1 μM, at least about 0.1 mM, at least about 1 mM, etc., as is known in the art. The reaction can be performed using commercial sources of copper(I) such as cuprous bromide or iodide or a compound such as tetrakis(acetonitrile)copper(l)hexafluorophosphate as long as the reaction is performed under anaerobic conditions. The reaction can be run in a variety of solvents, and mixtures of water and a variety of (partially) miscible organic solvents including alcohols, DMSO, DMF, tBuOH and acetone work well. The reaction will proceed at room temperature, and is allowed to proceed to the desired level of completion, e.g. at least about 15 minutes, at least about one hour, at least about 4 hours, at least about 8 hours, or more.

The invention further provides nucleic acids encoding the foldon polypeptides of the invention. As will be appreciated by those in the art, due to the degeneracy of the genetic code, an extremely large number of nucleic acids may be made, all of which encode the foldon polypeptides of the present invention. Thus, having identified a particular amino acid sequence, those skilled in the art could make any number of different nucleic acids, by simply modifying the sequence of one or more codons in a way that does not change the amino acid sequence.

Using the nucleic acids of the present invention that encode a foldon polypeptide including without limitation various fusion proteins, a variety of expression constructs can be made. The expression constructs may be self-replicating extrachromosomal vectors or vectors which integrate into a host genome. Alternatively, for purposes of cell-free expression the construct may include those elements required for transcription and translation of the desired polypeptide, but may not include such elements as an origin of replication, selectable marker, etc. Cell-free constructs may be replicated in vitro, e.g. by PCR, and may comprise terminal sequences optimized for amplification reactions.

Generally, expression constructs include transcriptional and translational regulatory nucleic acid operably linked to the nucleic acid encoding the fusion protein. The term “control sequences” refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is “operably linked” when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, “operably linked” means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in in vitro expression systems, such as the T7 promoter.

In addition, the expression construct may comprise additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Cell-Free Synthesis

In some embodiments of the invention, the foldon polypeptide is produced by cell-free, or in vitro synthesis, in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001, herein incorporated by reference. In some embodiments the reaction conditions are modified to improve formation of disulfide bonds, e.g. as set forth in U.S. Pat. No. 7,871,794, herein specifically incorporated by reference.

In one embodiment of the invention, the reaction chemistry is as described in co-pending patent application U.S. Ser. No. 10/643,683, filed Aug. 18, 2003, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a system homeostatic in $[PO_4]$ and pH, in which synthesis can occur even in the absence of secondary energy sources.

The template for cell-free protein synthesis can be either mRNA or DNA. Translation of stabilized mRNA or combined transcription and translation converts stored information into protein. The combined system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally between pH 6 and pH 9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome of the extract source cells.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may be large scale, small scale, or may be multiplexed to perform a plurality of simultaneous syntheses. Additional reagents may be introduced to prolong the period of time for active synthesis. Synthesized product is usually accumulated in the reactor and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include *E. coli* extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, putrescine, spermine, spermidine, etc.

The salts preferably include potassium, magnesium, and ammonium salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine or optionally, in combination, putrescine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

Formulations and Uses

The foldon polypeptides, including foldon fusion proteins and particles comprising such proteins may be provided in a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Other formulations include suitable delivery forms known in the art including, but not limited to, carriers such as liposomes. Mahato et al. (1997) Pharm. Res. 14:853-859. Liposomal preparations include, but are not limited to, cytofectins, multilamellar vesicles and unilamellar vesicles.

Generally, these compositions are formulated for administration by injection or inhalation, e.g., intraperitoneally, intravenously, subcutaneously, intramuscularly, etc. Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention.

The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

The foldon monomer derived from the base of the T4 bacteriophage tailspike protein assembles into a trimer by forming intermolecular hydrogen bonds (FIG. 1). Therefore, the foldon can be used to assist a fused polypeptide to form a homotrimer when it is fused to the N-terminus or C-terminus of the target protein.

Figure 2:
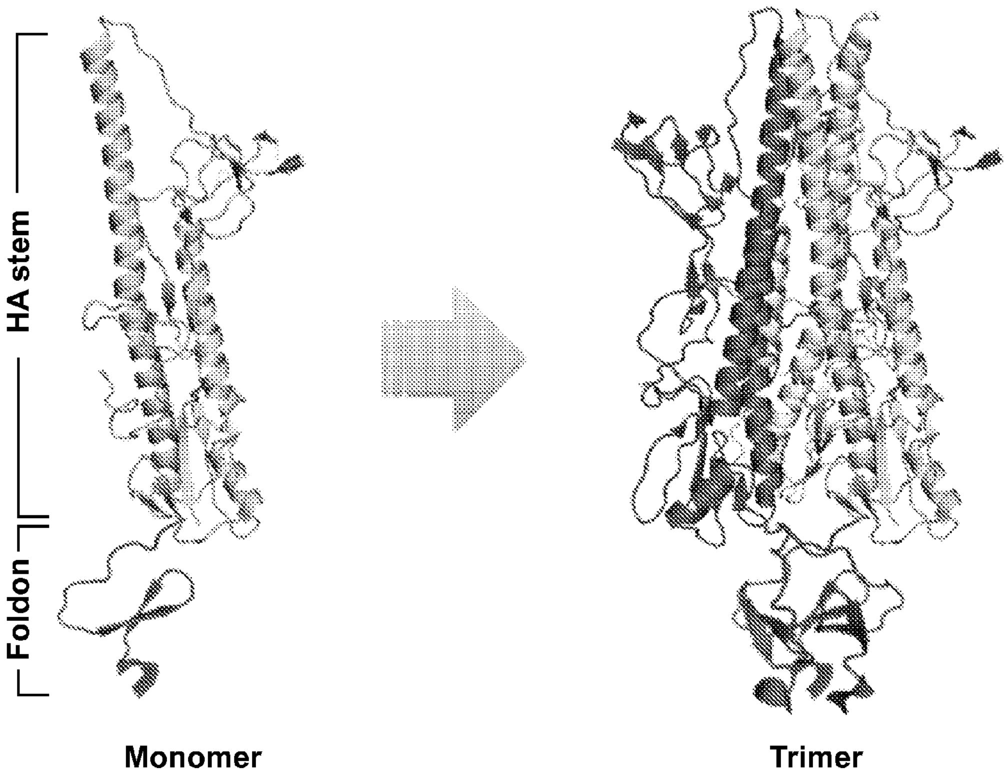
FIG. 2 Trimerization of HA stem domain with the help of the foldon polypeptide.

Using an influenza hemagglutinin (HA) stem domain protein as an example, the foldon domain was fused to the C-terminus of the HA stem domain to induce trimerization (FIG. 2).

Figure 3:
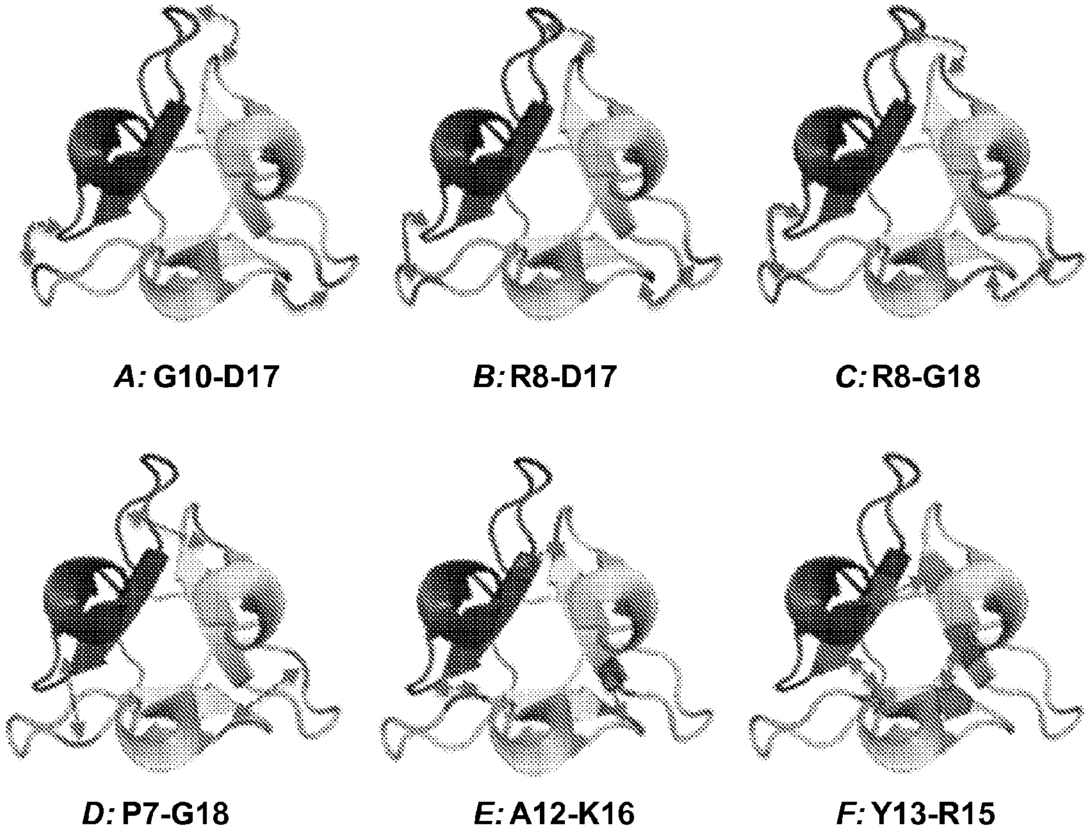
FIG. 3 Candidate mutations estimated to result in intermolecular disulfide bond formation.
Figure 4:
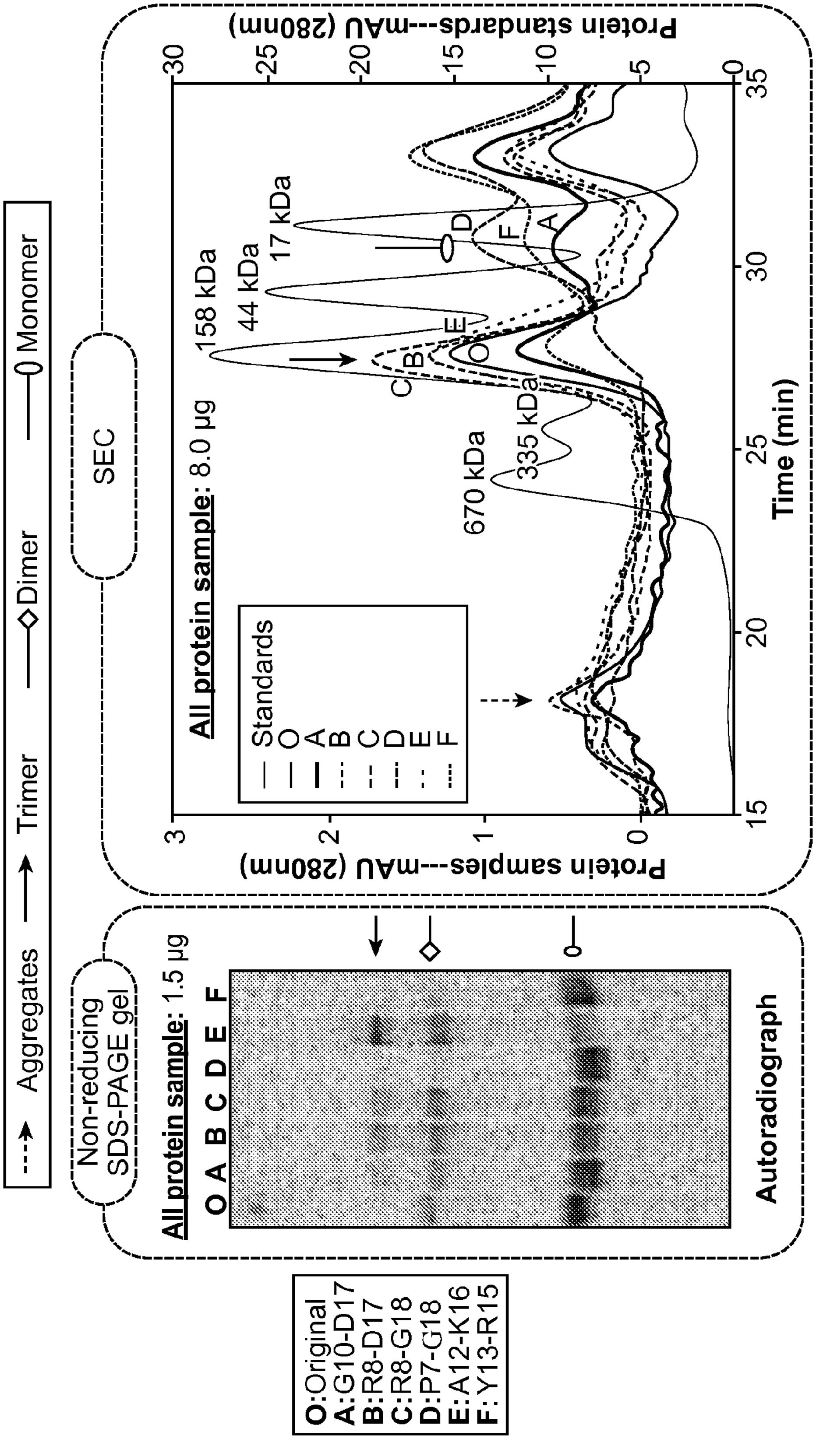
FIG. 4 Comparison of different foldon mutants using SDS-PAGE and size-exclusion HPLC.

However, due to changes in the physical environment (pH, buffer, ionic strength, excipients, etc.), the hydrogen bonds in the foldon trimer might be weakened, and the trimer could dissociate into the monomer. To stabilize the HA stem trimer, we artificially introduced new cysteine residues to potentially form intermolecular disulfide bonds between foldon monomers. Disulfide bonds are much stronger than hydrogen bonds. Since we intended to conjugate the HA stem trimer to the surface of VLPs and since the covalent attachment bond will only be through one monomer out of the three monomers in the trimer, it is particularly important to stabilize the trimer with intermolecular covalent bonds to avoid the disassembly of the stem trimer during vaccine preparation and administration. We introduced cysteines at the following locations to evaluate which pairs could form intermolecular disulfide bonds (G10-D17, R8-D17, R8-G18, P7-G18, A12-K16 and Y13-R15) as shown in FIG. 3. SDS-PAGE results (FIG. 4) showed that design A, B, C and E all can form the trimer with intermolecular S—S bonds between foldon monomers. Version E enabled the best formation of disulfide linked trimer. Size-exclusion HPLC results (FIG. 4) showed that the formation of the foldon trimer was hindered with mutations A, D and F.

Figure 5:
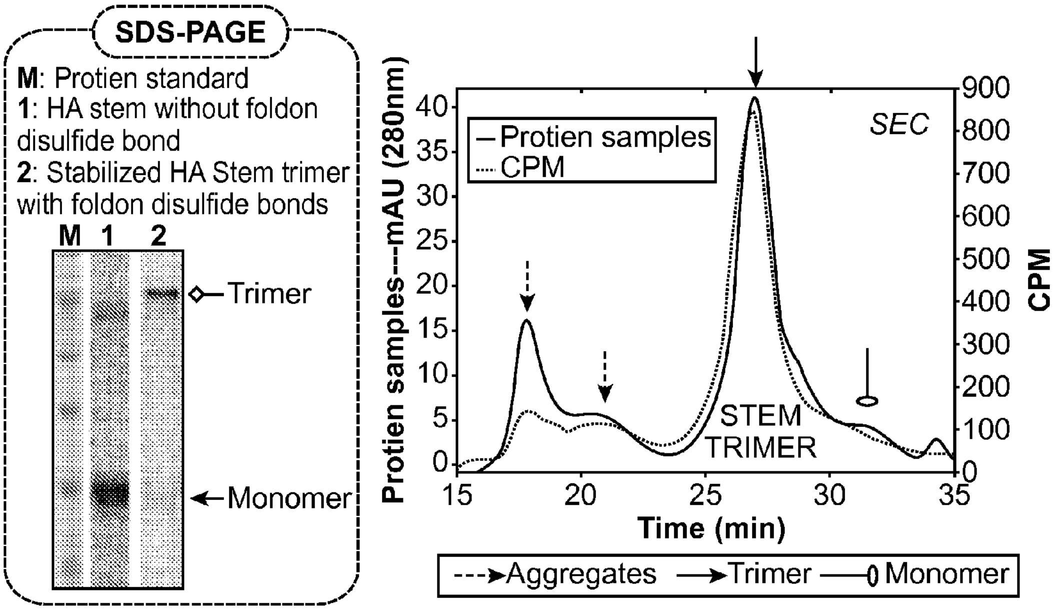
FIG. 5 Analysis of HA stem trimer after optimizing the refolding conditions, by using SDS-PAGE and size-exclusion HPLC.

To increase the proportion of trimer and the completeness of intermolecular disulfide bond formation, the refolding conditions were modified. We used Cystamine and Cysteamine as the "oxido-shuffling" reagent. The composition of the modified refolding buffer was: 50 mM Tris-HCl; 600 mM Arginine; 2 mM EDTA; Cystamine/Cysteamine (1:20); 0.05% Brij35; pH=8. We also found that the removal of oxygen from the refolding buffer was helpful for the formation of the trimer and the desired disulfide bonds. After optimizing the refolding conditions, the proportion of trimer can reach around 75% by the analysis of SDS-Size-exclusion HPLC (FIG. 5, right). The formation of intermolecular disulfide bonds is nearly complete as indicated by SDS PAGE analysis (FIG. 5, left).

Figure 6:
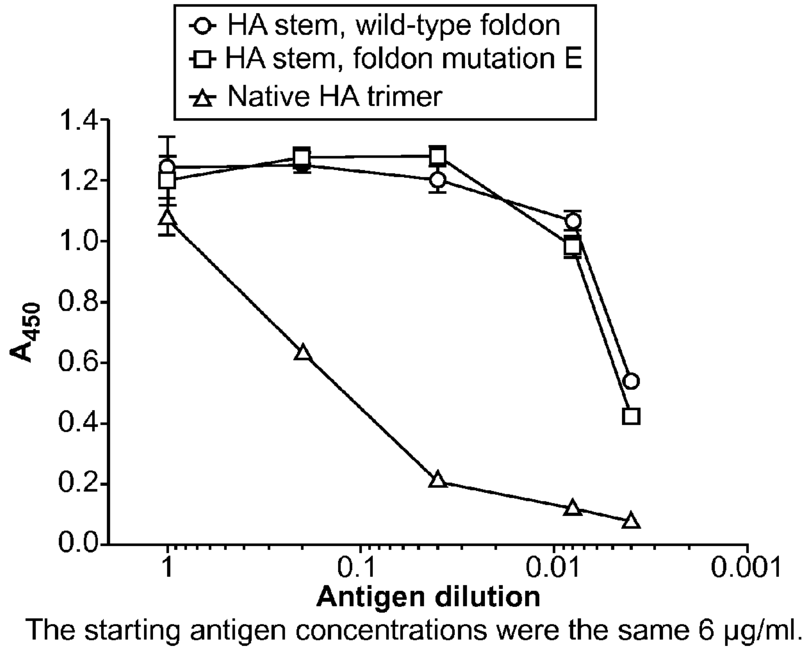
FIG. 6 ELISA analysis of HA stem with wild-type foldon and with foldon mutation E, by using antibody C179.

The correct immunogenic conformation of this stabilized HA stem trimer (with foldon mutation E) was confirmed using a commercial antibody C179 that blocks influenza infection by binding to the HA stem trimer. As shown in FIG. 6, the foldon mutation E with disulfide bonds did not affect the function of the HA stem trimer, and the stabilized HA stem trimer was much better than native HA trimer.

Materials and Methods

Construction of a fusion protein with a disulfide stabilized foldon domain. As an example, a fusion was made to a (HA) stem domain protein. The 27aa foldon polypeptide was fused to the C-terminus of the HA stem domain to induce trimerization. The DNA that codes for the fusion protein was cloned into the pY71 vector using NdeI and SalI restriction sites (Kuchenreuther et al., 2009). The amino acid sequence of the fusion protein was as follows:

(SEQ ID NO: 8)

MDTLCIGYHANNSTDTVDTVLEKNVTVTHSVNLLEDKGSGSGTSLPFQ

NIHPITIGKTPKYVKSTKLRLATGLRNVPSIQSRGLFGAIAGFIEGGW

TGMVDGWYGYHHQNEQGSGYAADLKSTQNAIDEITNKVNSVIEKMNTQ

DTAVGKEFNHDEKRIENLNKKVDDGFLDIWTYNAELLVLLENERTLDY

HDSNVKNLYEKVRSQLKNNAKEIGNGCFEFYHKCDNTCMESVKNGTYD

YPKYSEEAKLNREEIDGVgsgsgsgsGYIPEAPRDGQAYVRKDGEWVL

LSTFLggsgsgsgHHHHHH

The nucleotide sequence encoding the fusion protein was as follows:

(SEQ ID NO: 9)

ATGGATACCCTCTGCATTGGTTACCACGCGAACAACTCCACCGATACC

GTTGACACTGTTCTCGAAAAGAACGTGACCGTGACTCACTCTGTGAAC

CTGCTGGAAGACAAAGGTTCTGGCTCTGGTACCTCTCTCCCATTCCAG

AACATCCATCCAATCACCATTGGCAAGACTCCAAAGTATGTTAAGTCT

ACCAAACTCCGCCTGGCTACCGGTCTGCGCAATGTTCCGTCTATTCAG

TCCCGTGGTCTGTTCGGCGCTATTGCTGGCTTCATCGAGGGCGGCTGG

ACTGGTATGGTTGACGGCTGGTACGGCTACCATCACCAGAACGAACAA

GGCTCTGGCTATGCGGCGGACCTGAAATCTACTCAAAATGCTATCGAC

GAAATCACTAATAAGGTTAATTCCGTGATCGAAAAAATGAATACTCAG

GACACTGCGGTTGGTAAAGAATTCAACCACGACGAGAAGCGTATTGAG

AATCTGAACAAAAAAGTGGACGACGGTTTTCTCGACATCTGGACCTAT

AACGCGGAACTGCTCGTGCTCCTGGAGAATGAACGTACCCTGGATTAC

CATGATTCTAATGTGAAGAATCTCTATGAGAAAGTTCGCTCTCAGCTC

AAAAACAATGCGAAAGAAATCGGTAATGGTTGCTTCGAATTCTACCAC

AAATGTGACAATACCTGCATGGAATCCGTTAAGAACGGTACCTACGAC

TACCCAAAATACTCTGAAGAAGCGAAACTGAACCGCGAAGAGATCGAT

GGCGTGggttctggctctggttctggttctGGTTACATCCCGGAAGCT

CCGCGTGACGGTCAGGCGTACGTTCGTAAAGACGGTGAATGGGTTCTG

-continued

CTGTCTACCTTCCTGggtggttctggctctggttctggcCACCACCAT

CATCACCACTAA

CAPS represent the HA stem domain protein. Lower case represents the linker peptide. Underlined CAPS represent the foldon domain. BOLD CAPS represent the $His_6$ tag.

Pairs of cysteines were introduced into the foldon domain at six different locations to form intermolecular disulfide bonds. The codon changes were affected using the QuikChange procedure (Stratagene). Six different foldon mutants are shown in Table 2.

TABLE 1

The sequences of six different foldon mutants

| Mutation positions | Foldon sequence* | Coding sequence* |
|---|---|---|
| Original SEQ ID NO: 1 | GYIPEAPRDGQAYVRKDGE WVLLSTFL | GGTTACATCCCGGAAGCTCCGCGTGACGGTCAGGCGTA CGTTCGTAAAGACGGTGAATGGGTTCTGCTGTCTACCT TCCTG SEQ ID NO: 14 |
| A: G10C-D17C SEQ ID NO: 2 | GYIPEAPRDCQAYVRKCGE WVLLSTFL | GGTTACATCCCGGAAGCTCCGCGTGACTGTCAGGCGTA CGTTCGTAAATGCGGTGAATGGGTTCTGCTGTCTACCT TCCTG SEQ ID NO: 15 |
| B: R8C-D17C SEQ ID NO: 3 | GYIPEAPCDGQAYVRKCGE WVLLSTFL | GGTTACATCCCGGAAGCTCCGTGTGACGGTCAGGCGTA CGTTCGTAAATGCGGTGAATGGGTTCTGCTGTCTACCT TCCTG SEQ ID NO: 16 |
| C: R8C-G18C SEQ ID NO: 4 | GYIPEAPCDGQAYVRKDCE WVLLSTFL | GGTTACATCCCGGAAGCTCCGTGTGACGGTCAGGCGTA CGTTCGTAAAGACTGTGAATGGGTTCTGCTGTCTACCT TCCTG SEQ ID NO: 17 |
| D: P7C-G 18C SEQ ID NO: 5 | GYIPEACRDGQAYVRKDCE WVLLSTFL | GGTTACATCCCGGAAGCTTGCCGTGACGGTCAGGCGTA CGTTCGTAAAGACTGTGAATGGGTTCTGCTGTCTACCT TCCTG SEQ ID NO: 18 |
| E: A12C-K16C SEQ ID NO: 6 | GYIPEAPRDGQCYVRCDGE WVLLSTFL | GGTTACATCCCGGAAGCTCCGCGTGACGGTCAGTGCTA CGTTCGTTGCGACGGTGAATGGGTTCTGCTGTCTACCT TCCTG SEQ ID NO: 19 |
| F: Y13C-R15C SEQ ID NO: 7 | GYIPEAPRDGQACVCKDGE WVLLSTFL | GGTTACATCCCGGAAGCTCCGCGTGACGGTCAGGCGTG CGTTTGTAAAGACGGTGAATGGGTTCTGCTGTCTACCT TCCTG SEQ ID NO: 20 |

*Underlined represents mutated sequence.

Cell-Free Protein Synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 13.3 μg/mL plasmid, approximately 100-300 μg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of *E. coli* KC6 S30 extract (Goerke and Swartz 2008; Knapp et al. 2007). All reagents were obtained from Sigma-Aldrich (St. Louis, Mo.) unless otherwise noted.

Several modifications to PANOx-SP CFPS were made to encourage disulfide bond formation. First, the cell extract was pretreated at room temperature for 1 h with 1 mM iodoacetamide (IAM). Prior to template DNA addition, a glutathione buffer (4 mM oxidized glutathione and 1 mM reduced glutathione, unless otherwise specified) was added to the cell-free reaction to stabilize the thiol/disulfide redox potential. Finally, DsbC, a periplasmic disulfide bond isomerase, was added to a final concentration of 100 μg/mL.

CFPS reactions to produce the fusion protein were conducted at 30° C. for 6 h. Small-scale CFPS reactions were carried out in 20 μL volumes in 1.5 mL microcentrifuge tubes. Preparative-scale reactions used 6 mL volumes with 1 mL per well in 6-well tissue culture plates (BD Falcon #3046, BD, Franklin Lakes, N.J.). 8.4 μM L-[U-$^{14}$C]-Leucine (Perkin Elmer, Waltham, Mass.) was added to small-scale reactions and to 20 μL aliquots of preparative-scale reactions for measuring protein yields using a previously described trichloroacetic acid protocol (Calhoun and Swartz 2005) and a Beckman LS3801 liquid scintillation counter (Beckman Coulter, Fullerton, Calif.). The soluble fraction of preparative-scale reactions was recovered by centrifugation at 21,000×g, 15 min for further evaluation and purification.

Protein purification and refolding. After the CFPS reaction, the insoluble inclusion bodies were washed and dissolved in denaturing buffer. The pure inclusion bodies were then purified and refolded. The buffers used in the dissolving, purification and refolding process were as follows:

Washing buffer I: 50 mM Tris-HCl; 100 mM NaCl; 1 mM EDTA; pH=8

Washing buffer II: 100 mM $NaH_2PO_4$; 10 mM Tris-HCl; 20 mM Imidazole; pH=8

Denaturing washing buffer: 8M Urea; 100 mM $NaH_2PO_4$; 10 mM Tris-HCl; 20 mM Imidazole; 1 mM DTT; pH=8

Denaturing elution buffer: 8M Urea; 100 mM $NaH_2PO_4$; 10 mM Tris-HCl; 500 mM Imidazole; 1 mM DTT; pH=8

Denaturing buffer: 8M Urea; 50 mM Tris-HCl; 2 mM EDTA; 1 mM DTT; pH=8

Refolding buffer: 50 mM Tris-HCl; 600 mM Arginine; 2 mM EDTA; Cystamine/Cysteamine (0.5:5 mM); 0.05% Brij35; pH=8

Dialysis buffer: 50 mM Tris-HCl; 100 mM Arginine; 0.05% Brij35; pH=8

Figure 10:
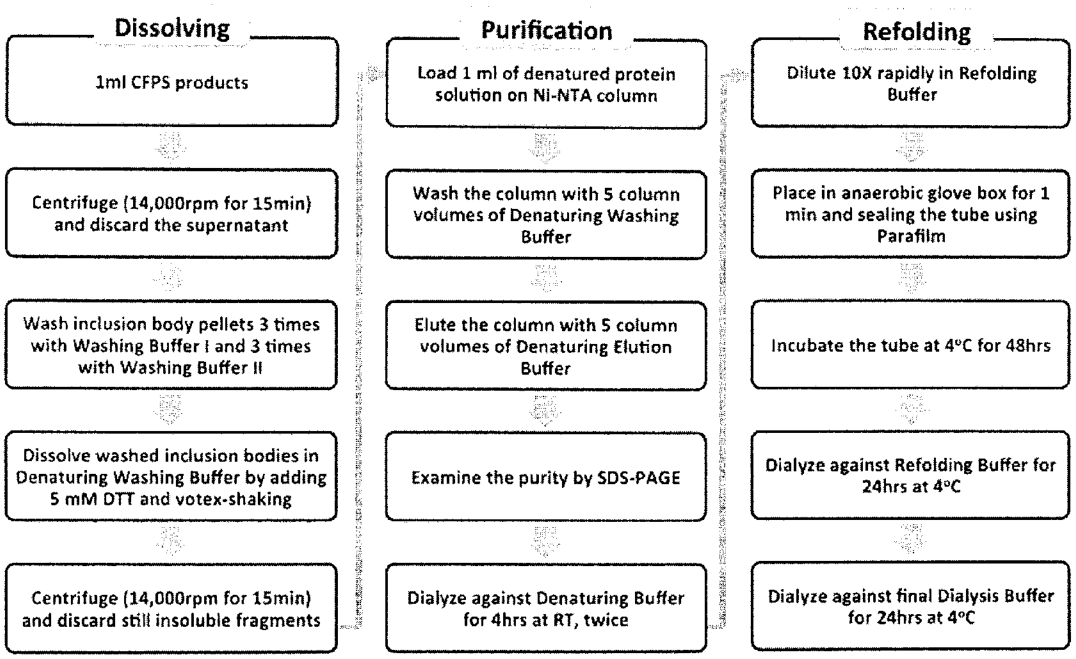
FIG. 10 Flow Diagram of Protein purification and refolding process.

All the procedures are shown in the flow diagram of FIG. 10.

Size Exclusion HPLC. Refolded proteins were tested on a Ultrahydrogel 500 HPLC column, 300 mm×7.8 mm inner diameter with 10 μM particles (Waters). The running buffer was 50 mM Tris-HCl (pH 8.0), 500 mM Arginine, 0.05% Brij 35, pumped at 0.3 mL/min. The injection volume was 80 μL. Protein absorbance was monitored in-line at 280 nm over a period of 60 min.

ELISA binding of HA stem constructs. In an enzyme-linked immunosorbent assay (ELISA), 50 μL of antibody C179 (Mouse IgG) (TAKAR Bio INC.) at 2 μg/mL concentrations were coated on 96-well ELISA plates (Microlon, flat-bottom, high binding; Greiner Bio One, Frickenhausen, Germany) and allowed to bind overnight at 4° C. Commercial HA consisted of amino acids 18-529 of the 2009 H1 N1 strain (HA(ΔTM)(A/California/07/2009(H1N1); Immune Technology Corp., New York, N.Y.). Plates were then washed three times with wash buffer (PBS buffer with 0.1% Tween-20) and blocked with PBS buffer with 3% bovine serum albumin (blocking buffer) and placed at 37° C. for 1 h. After washing four times with wash buffer, 50 μL dilutions of 6 μg/mL commercial HA protein and refolded HA stem domain protein were then added to the plates and incubated at 37° C. for 1 h. Plates were again washed three times with wash buffer before adding 1 μg/mL of monoclonal anti-his biotin-conjugated antibody in blocking buffer and incubating at 37° C. for 1 h. Plates were again washed three times with wash buffer before adding peroxidase-conjugated anti-biotin antibody at a 1:1000 dilution in blocking buffer and incubating at 37° C. for 1 h. Plates were again washed six times before developing with 50 μL of TMB substrate (KPL) and quenching with 30 μL of 2% $H_2SO_4$. Each well was measured at $OD_{450}$ with an ELISA plate reader. Each data point indicates the mean of triplicate assay results and error bars represent standard deviation.

Example 2

The foldon monomer derived from the base of the T4 bacteriophage tailspike protein assembles into a trimer by forming intermolecular hydrogen bonds. Therefore, the foldon can be used to assist a fused polypeptide to form a homotrimer when it is fused to the N-terminus or C-terminus of the target protein.

Figure 7:
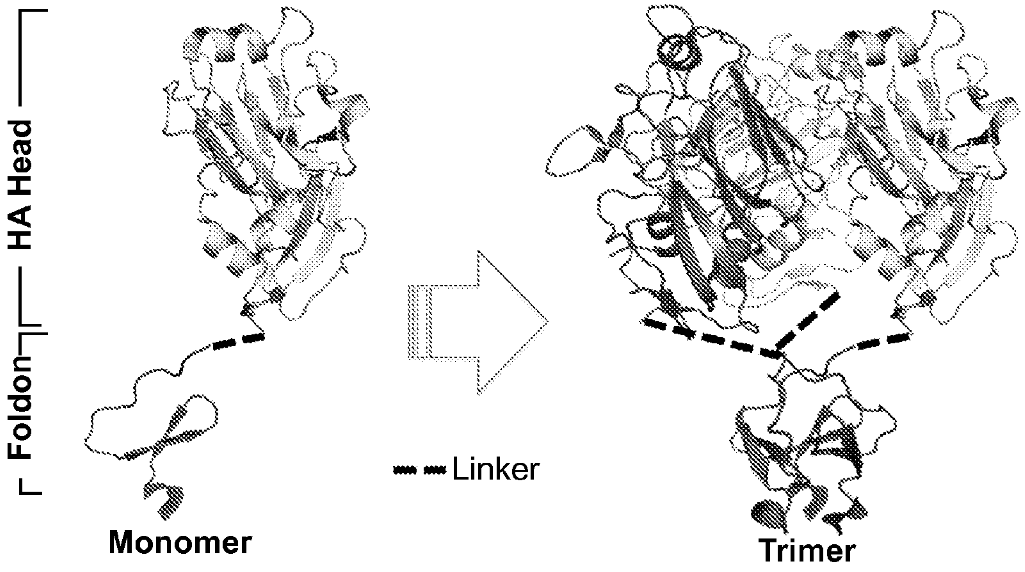
FIG. 7 Trimerization of HA head domain with the help of the foldon polypeptide.
Figure 8:
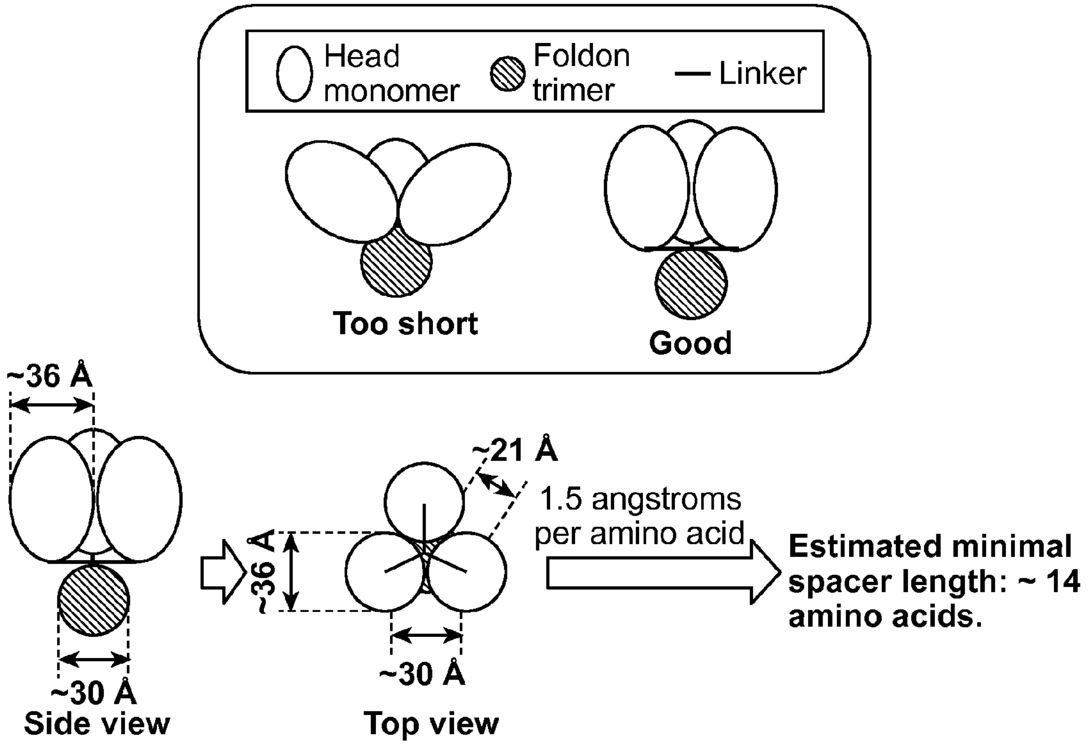
FIG. 8 A simple estimation of spacer length between HA head trimer and foldon trimer.

The disulfide stabilized foldon was then evaluated for inducing the trimerization of the HA head domain (FIG. 7). However, the linker and foldon construction used for the stem trimer did not allow the head group to form the required trimeric form. We therefore modified the overall design of the trimerization domain including the foldon and the polypeptide linker. The protein structure of the head region of the full HA trimer was used to estimate the regional linker length. Based on the size of HA head domain and foldon trimer, the appropriate spacer length was estimated to be ~21 angstroms (FIG. 8). Each amino acid spans around 1.5 angstroms, so that is approximately at least 21/1.5=14 amino acids. Various linker sequences find use for this purpose, for example (e.g., $(GS)_n$, $(G_4S)_n$, $(GSA)_n$, SEQ ID NO:13 $A(EAAAK)_nA$ and $(AP)_n$), provided that the length is appropriate.

SEQ ID NO:21 $GSGSGS(GGGGS)_2GS$ was selected as an example. To stabilize the foldon sequence, cysteines were evaluated at the following locations in the foldon sequence to determine if one of the pairs (G10-D17, R8-D17, R8-G18, P7-G18, A12-K16 and Y13-R15; shown in Table 1) could form correct intermolecular disulfide bonds to induce and stabilize trimerization of the HA head domain.

Figure 9:
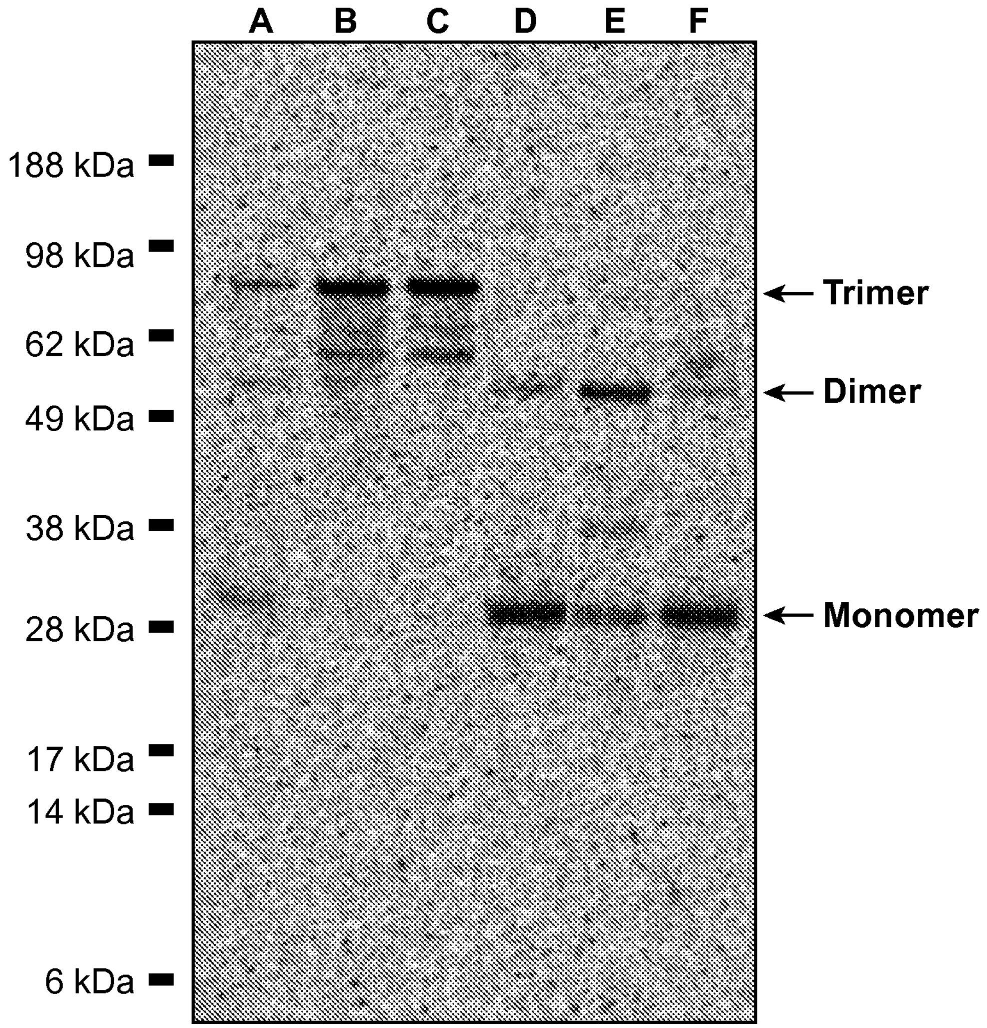
FIG. 9 Comparison of different foldon mutants using SDS-PAGE.

As shown in FIG. 9, SDS-PAGE results showed that design B and C both could form the trimer with correct intermolecular S—S bonds between foldon monomers. Design C was a little better than design B. Therefore, foldon version C was the best for stabilizing the trimerization of HA head domain. However, as shown in Example 1, foldon version E was the best for the HA stem domain. Thus, reasonable experimentalism can be used to determine the best cysteine pair locations from the variants set forth in Table 1 for forming and stabilizing trimer forms of fusion partners.

Materials and Methods

Construction of fusion protein with foldon domain. We used a hemagglutinin (HA) head domain protein. The 27aa foldon polypeptide was fused to the C-terminus of the HA head domain to induce trimerization. The DNA that codes for the fusion protein was cloned into the pY71 vector using NdeI and AatII restriction sites (Kuchenreuther et al., 2009). The amino acid sequence of the fusion protein was as follows, where the foldon sequence is underlined and the linker is shown in lower case:

(SEQ ID NO: 10)

```
MKCNIAGWILGNPECESLSTASSWSYIVETSSSDNGTCYPGDFIDYEE
LREQLSSVSSFERFEIFPKTSSWPNHDSNKGVTAACPHAGAKSFYKNL
IWLVKKGNSYPKLSKSYINDKGKEVLVLWGIHHPSTSADQQSLYQNAD
AYVFVGSSRYSKKFKPEIAIRPKVRDQEGRMNYYWTLVEPGDKITFEA
TGNLVVPRYAFALERNAGSGSGSSgsgsgsggggsggggsgsGYIPEA
PCDGQAYVRKDCEWVLLSTFLGgggggsWSHPQFEK
```

The nucleotide sequence encoding the fusion protein was as follows:

(SEQ ID NO: 11)

```
ATGAAATGCAACATCGCTGGTTGGATTCTGGGCAACCCGGAGTGCGAG
TCCCTCTCCACTGCGTCCTCTTGGTCTTACATCGTTGAAACTTCTTCT
TCCGATAATGGTACTTGCTATCCAGGTGATTTTATCGACTACGAAGAA
CTCCGTGAGCAACTCTCTTCTGTGTCTTCTTTTGAACGCTTTGAGATC
TTTCCGAAAACCTCTTCTTGGCCGAACCACGATTCCAATAAAGGCGTT
ACCGCGGCTTGCCCACACGCTGGTGCGAAATCTTTCTACAAAAACCTG
ATCTGGCTCGTGAAAAAGGGTAATTCCTACCCGAAGCTCTCTAAGTCC
TACATCAACGACAAAGGCAAAGAAGTGCTGGTTCTGTGGGGCATCCAC
CACCCATCTACCTCTGCGGACCAGCAGTCCCTGTACCAGAATGCTGAT
GCTTACGTTTTCGTTGGCTCTTCTCGCTACTCCAAGAAATTCAAACCG
GAAATTGCGATTCGCCCAAAGGTTCGTGACCAGGAAGGTCGTATGAAC
TACTACTGGACCCTGGTGGAACCGGGCGACAAGATTACCTTTGAGGCG
ACCGGCAACCTGGTTGTTCCACGCTATGCTTTCGCGCTGGAACGTAAC
GCTGGCTCCGGTAGCGGCAGCTCTggttctggctctggttctggcggt
ggtggctctggtggcggtggctctggttctGGTTACATCCCGGAAGCT
CCGCGTGACGGTCAGGCGTACGTTCGTAAAGACGGTGAATGGGTTCTG
```

-continued

CTGTCTACCTTCCTGGGTggaggaggtggctccTGGAGCCACCCGCAG

TTCGAAAAGTAA

CAPS represent the HA head domain protein. Lower case represents the linker peptide. Underlined CAPS represent the foldon domain. BOLD CAPS represent the Strep II tag.

Pairs of cysteines were introduced into the foldon domain at six different locations to form intermolecular disulfide bonds. The codon changes were affected using the QuikChange procedure (Stratagene). Six different foldon mutants are shown in Example 1, Table 1.

Cell-Free Protein Synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 13.3 μg/mL plasmid, approximately 100-300 μg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of *E. coli* KGK10 extract (Goerke and Swartz 2008; Knapp et al. 2007). All reagents were obtained from Sigma-Aldrich (St. Louis, Mo.) unless otherwise noted.

Several modifications to PANOx SP CFPS were made to encourage disulfide bond formation. First, the cell extract was pretreated at room temperature for 1 h with 50 μM iodoacetamide (IAM). Prior to template DNA addition, a glutathione buffer (4 mM oxidized glutathione and 1 mM reduced glutathione, unless otherwise specified) was added to the cell-free reaction to stabilize the thiol/disulfide redox potential. Finally, DsbC, a periplasmic disulfide bond isomerase, was added to a final concentration of 100 μg/mL.

CFPS reactions to produce the fusion protein were conducted at RT for 12 h. Small-scale CFPS reactions were carried out in 20 μL volumes in 1.5 mL microcentrifuge tubes. Preparative-scale reactions used 6 mL volumes with 1 mL per well in 6-well tissue culture plates (BD Falcon #3046, BD, Franklin Lakes, N.J.). 8.4 μM L-[U-$^{14}$C]-Leucine (PerkinElmer, Waltham, Mass.) was added to small-scale reactions and to 20 μL aliquots of preparative-scale reactions for measuring protein yields using a previously described trichloroacetic acid protocol (Calhoun and Swartz 2005) and a Beckman LS3801 liquid scintillation counter (Beckman Coulter, Fullerton, Calif.). The soluble fraction of preparative-scale reactions was recovered by centrifugation at 21,000×g, 15 min for further evaluation and purification.

Protein purification. Soluble CFPS products from 3 mL reactions were purified using Strep-tag II/Strep-tactin affinity chromatography (IBA Gmbh, Gottingen, Germany). The soluble fractions of the CFPS solution were applied to a 1.0 mL Strep-Tactin gravity flow column (IBA Gmbh) and washed with 10 mL of PBS buffer (pH 7.4). The loaded column was eluted with PBS buffer containing 5.0 mM desthiobiotin, and 0.5 mL fractions were analyzed for protein content using SDS PAGE gels. Pooled fractions were then dialyzed against PBS buffer to remove the desthiobiotin and stored at 4° C.

SDS-PAGE gel analysis. Protein size was analyzed by SDS-PAGE gel and autoradiography. NuPAGE Novex precast gels and reagents were purchased from Invitrogen (Carlsbad, Calif.). Samples were mixed with LDS running buffer. The samples were loaded onto a 10% (w/v) Bis-Tris precast gel using the SeeBlue Plus2 molecular weight standard, and the electrophoresis was conducted using the MES running buffer (Invitrogen). SimplyBlue SafeStain (Invitrogen) was used to stain and fix the gels according to the manufacturer's recommendations. The gels were dried using a gel dryer model 583 (Bio-Rad, Richmond, Calif.), before exposure to storage phosphor screen (Molecular Dynamics), which was subsequently scanned using a Typhoon Scanner (GE Healthcare).

What is claimed is:

1. A cysteine-substituted foldon polypeptide, wherein two amino acids of a native foldon polypeptide are substituted with cysteine residues that can form intermolecular disulfide bonds when the foldon is in a trimeric quaternary structure, wherein the native foldon polypeptide has the amino acid sequence set forth in SEQ ID NO:1 and wherein the amino acid substitutions are selected from [G10C, D17C]; [R8C, D17C]; [R8C, G18C]; [P7C, G18C]; [A12C, K16C]; and [Y13C, R15C].

2. The cysteine-substituted foldon polypeptide of claim 1, wherein the amino acid substitutions are selected from [A12C, K16C]; [R8C, D17C]; and [R8C, G18C].

3. The cysteine-substituted foldon polypeptide of claim 1, wherein the cysteine-substituted foldon polypeptide is a monomer.

4. The cysteine-substituted foldon polypeptide of claim 1, wherein the cysteine-substituted foldon polypeptide is a trimer.

5. The cysteine-substituted foldon polypeptide of claim 1, wherein the cysteine-substituted foldon polypeptide is joined to a fusion partner.

6. The cysteine-substituted foldon polypeptide of claim 5, wherein the fusion partner is a viral antigen.

7. The cysteine-substituted foldon polypeptide of claim 1, further comprising one or more of a tag for purification, an unnatural amino acid, and site for protease cleavage.

8. The cysteine-substituted foldon polypeptide of claim 7, wherein the cysteine-substituted foldon polypeptide is a fusion protein, and comprises at least one unnatural amino acid at a defined site.

9. The cysteine-substituted foldon polypeptide of claim 8, where the cysteine-substituted foldon polypeptide is a trimer, and the unnatural amino acid is used to covalently join one chain of the trimer to a virus like particle.

10. A method of producing a cysteine-substituted foldon polypeptide according to claim 1, comprising introducing a polynucleotide sequence encoding the cysteine-substituted foldon polypeptide operably linked to a promoter, into a cell or cell free protein synthesis reaction mix and incubating for a period of time sufficient to synthesize the protein.

* * * * *

SEQUENCE LISTING

<160> NUMBER OF SEQ ID NOS: 21

<210> SEQ ID NO 1
<211> LENGTH: 27
<212> TYPE: PRT
<213> ORGANISM: T4 bacteriophage

<400> SEQUENCE: 1

Gly Tyr Ile Pro Glu Ala Pro Arg Asp Gly Gln Ala Tyr Val Arg Lys
1 5 10 15

Asp Gly Glu Trp Val Leu Leu Ser Thr Phe Leu
20 25

<210> SEQ ID NO 2
<211> LENGTH: 27
<212> TYPE: PRT
<213> ORGANISM: T4 bacteriophage

<400> SEQUENCE: 2

Gly Tyr Ile Pro Glu Ala Pro Arg Asp Cys Gln Ala Tyr Val Arg Lys
1 5 10 15

Cys Gly Glu Trp Val Leu Leu Ser Thr Phe Leu

-continued 20 25

<210> SEQ ID NO 3
<211> LENGTH: 27
<212> TYPE: PRT
<213> ORGANISM: T4 bacteriophage

<400> SEQUENCE: 3

Gly Tyr Ile Pro Glu Ala Pro Cys Asp Gly Gln Ala Tyr Val Arg Lys
1 5 10 15

Cys Gly Glu Trp Val Leu Leu Ser Thr Phe Leu
20 25

<210> SEQ ID NO 4
<211> LENGTH: 27
<212> TYPE: PRT
<213> ORGANISM: T4 bacteriophage

<400> SEQUENCE: 4

Gly Tyr Ile Pro Glu Ala Pro Cys Asp Gly Gln Ala Tyr Val Arg Lys
1 5 10 15

Asp Cys Glu Trp Val Leu Leu Ser Thr Phe Leu
20 25

<210> SEQ ID NO 5
<211> LENGTH: 27
<212> TYPE: PRT
<213> ORGANISM: T4 bacteriophage

<400> SEQUENCE: 5

Gly Tyr Ile Pro Glu Ala Cys Arg Asp Gly Gln Ala Tyr Val Arg Lys
1 5 10 15

Asp Cys Glu Trp Val Leu Leu Ser Thr Phe Leu
20 25

<210> SEQ ID NO 6
<211> LENGTH: 27
<212> TYPE: PRT
<213> ORGANISM: T4 bacteriophage

<400> SEQUENCE: 6

Gly Tyr Ile Pro Glu Ala Pro Arg Asp Gly Gln Cys Tyr Val Arg Cys
1 5 10 15

Asp Gly Glu Trp Val Leu Leu Ser Thr Phe Leu
20 25

<210> SEQ ID NO 7
<211> LENGTH: 27
<212> TYPE: PRT
<213> ORGANISM: T4 bacteriophage

<400> SEQUENCE: 7

Gly Tyr Ile Pro Glu Ala Pro Arg Asp Gly Gln Ala Cys Val Cys Lys
1 5 10 15

Asp Gly Glu Trp Val Leu Leu Ser Thr Phe Leu
20 25

<210> SEQ ID NO 8
<211> LENGTH: 307
<212> TYPE: PRT
<213> ORGANISM: T4 bacteriophage

<400> SEQUENCE: 8

-continued

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys Gly Ser Gly Ser Gly Thr Ser Leu Pro Phe Gln
        35                  40                  45

Asn Ile His Pro Ile Thr Ile Gly Lys Thr Pro Lys Tyr Val Lys Ser
    50                  55                  60

Thr Lys Leu Arg Leu Ala Thr Gly Leu Arg Asn Val Pro Ser Ile Gln
65                  70                  75                  80

Ser Arg Gly Leu Phe Gly Ala Ile Ala Gly Phe Ile Glu Gly Gly Trp
                85                  90                  95

Thr Gly Met Val Asp Gly Trp Tyr Gly Tyr His His Gln Asn Glu Gln
            100                 105                 110

Gly Ser Gly Tyr Ala Ala Asp Leu Lys Ser Thr Gln Asn Ala Ile Asp
        115                 120                 125

Glu Ile Thr Asn Lys Val Asn Ser Val Ile Glu Lys Met Asn Thr Gln
    130                 135                 140

Asp Thr Ala Val Gly Lys Glu Phe Asn His Asp Glu Lys Arg Ile Glu
145                 150                 155                 160

Asn Leu Asn Lys Lys Val Asp Asp Gly Phe Leu Asp Ile Trp Thr Tyr
                165                 170                 175

Asn Ala Glu Leu Leu Val Leu Leu Glu Asn Glu Arg Thr Leu Asp Tyr
            180                 185                 190

His Asp Ser Asn Val Lys Asn Leu Tyr Glu Lys Val Arg Ser Gln Leu
        195                 200                 205

Lys Asn Asn Ala Lys Glu Ile Gly Asn Gly Cys Phe Glu Phe Tyr His
    210                 215                 220

Lys Cys Asp Asn Thr Cys Met Glu Ser Val Lys Asn Gly Thr Tyr Asp
225                 230                 235                 240

Tyr Pro Lys Tyr Ser Glu Glu Ala Lys Leu Asn Arg Glu Glu Ile Asp
                245                 250                 255

Gly Val Gly Ser Gly Ser Gly Ser Gly Ser Gly Tyr Ile Pro Glu Ala
            260                 265                 270

Pro Arg Asp Gly Gln Ala Tyr Val Arg Lys Asp Gly Glu Trp Val Leu
        275                 280                 285

Leu Ser Thr Phe Leu Gly Gly Ser Gly Ser Gly Ser Gly His His His
    290                 295                 300

His His His
305

<210> SEQ ID NO 9
<211> LENGTH: 924
<212> TYPE: DNA
<213> ORGANISM: T4 bacteriophage

<400> SEQUENCE: 9
atggataccc tctgcattgg ttaccacgcg aacaactcca ccgataccgt tgacactgtt 60
ctcgaaaaga acgtgaccgt gactcactct gtgaacctgc tggaagacaa aggttctggc 120
tctggtacct ctctcccatt ccagaacatc catccaatca ccattggcaa gactccaaag 180
tatgttaagt ctaccaaact ccgcctggct accggtctgc gcaatgttcc gtctattcag 240
tcccgtggtc tgttcggcgc tattgctggc ttcatcgagg gcggctggac tggtatggtt 300

-continued

```
gacggctggt acggctacca tcaccagaac gaacaaggct ctggctatgc ggcggacctg    360

aaatctactc aaaatgctat cgacgaaatc actaataagg ttaattccgt gatcgaaaaa    420

atgaatactc aggacactgc ggttggtaaa gaattcaacc acgacgagaa gcgtattgag    480

aatctgaaca aaaaagtgga cgacggtttt ctcgacatct ggacctataa cgcggaactg    540

ctcgtgctcc tggagaatga acgtaccctg gattaccatg attctaatgt gaagaatctc    600

tatgagaaag ttcgctctca gctcaaaaac aatgcgaaag aaatcggtaa tggttgcttc    660

gaattctacc acaaatgtga caatacctgc atggaatccg ttaagaacgg tacctacgac    720

tacccaaaat actctgaaga agcgaaactg aaccgcgaag agatcgatgg cgtgggttct    780

ggctctggtt ctggttctgg ttacatcccg gaagctccgc gtgacggtca ggcgtacgtt    840

cgtaaagacg gtgaatgggt tctgctgtct accttcctgg gtggttctgg ctctggttct    900

ggccaccacc atcatcacca ctaa                                          924
```

```
<210> SEQ ID NO 10
<211> LENGTH: 276
<212> TYPE: PRT
<213> ORGANISM: T4 bacteriophage

<400> SEQUENCE: 10

Met Lys Cys Asn Ile Ala Gly Trp Ile Leu Gly Asn Pro Glu Cys Glu
1               5                   10                  15

Ser Leu Ser Thr Ala Ser Ser Trp Ser Tyr Ile Val Glu Thr Ser Ser
            20                  25                  30

Ser Asp Asn Gly Thr Cys Tyr Pro Gly Asp Phe Ile Asp Tyr Glu Glu
        35                  40                  45

Leu Arg Glu Gln Leu Ser Ser Val Ser Ser Phe Glu Arg Phe Glu Ile
    50                  55                  60

Phe Pro Lys Thr Ser Ser Trp Pro Asn His Asp Ser Asn Lys Gly Val
65                  70                  75                  80

Thr Ala Ala Cys Pro His Ala Gly Ala Lys Ser Phe Tyr Lys Asn Leu
                85                  90                  95

Ile Trp Leu Val Lys Lys Gly Asn Ser Tyr Pro Lys Leu Ser Lys Ser
            100                 105                 110

Tyr Ile Asn Asp Lys Gly Lys Glu Val Leu Val Leu Trp Gly Ile His
        115                 120                 125

His Pro Ser Thr Ser Ala Asp Gln Gln Ser Leu Tyr Gln Asn Ala Asp
    130                 135                 140

Ala Tyr Val Phe Val Gly Ser Ser Arg Tyr Ser Lys Lys Phe Lys Pro
145                 150                 155                 160

Glu Ile Ala Ile Arg Pro Lys Val Arg Asp Gln Glu Gly Arg Met Asn
                165                 170                 175

Tyr Tyr Trp Thr Leu Val Glu Pro Gly Asp Lys Ile Thr Phe Glu Ala
            180                 185                 190

Thr Gly Asn Leu Val Val Pro Arg Tyr Ala Phe Ala Leu Glu Arg Asn
        195                 200                 205

Ala Gly Ser Gly Ser Gly Ser Ser Gly Ser Gly Ser Gly Ser Gly Gly
    210                 215                 220

Gly Gly Ser Gly Gly Gly Gly Ser Gly Ser Gly Tyr Ile Pro Glu Ala
225                 230                 235                 240

Pro Cys Asp Gly Gln Ala Tyr Val Arg Lys Asp Cys Glu Trp Val Leu
                245                 250                 255

Leu Ser Thr Phe Leu Gly Gly Gly Gly Gly Gly Ser Trp Ser His Pro
```

-continued

```
        260                 265                 270

Gln Phe Glu Lys
        275


<210> SEQ ID NO 11
<211> LENGTH: 828
<212> TYPE: DNA
<213> ORGANISM: T4 bacteriophage

<400> SEQUENCE: 11

atgaaatgca acatcgctgg ttggattctg ggcaacccgg agtgcgagtc cctctccact      60

gcgtcctctt ggtcttacat cgttgaaact tcttcttccg ataatggtac ttgctatcca     120

ggtgatttta tcgactacga agaactccgt gagcaactct cttctgtgtc ttcttttgaa     180

cgctttgaga tctttccgaa aacctcttct tggccgaacc acgattccaa taaaggcgtt     240

accgcggctt gcccacacgc tggtgcgaaa tctttctaca aaaacctgat ctggctcgtg     300

aaaaagggta attcctaccc gaagctctct aagtcctaca tcaacgacaa aggcaaagaa     360

gtgctggttc tgtggggcat ccaccaccca tctacctctg cggaccagca gtccctgtac     420

cagaatgctg atgcttacgt tttcgttggc tcttctcgct actccaagaa attcaaaccg     480

gaaattgcga ttcgcccaaa ggttcgtgac caggaaggtc gtatgaacta ctactggacc     540

ctggtggaac cgggcgacaa gattaccttt gaggcgaccg gcaacctggt tgttccacgc     600

tatgctttcg cgctggaacg taacgctggc tccggtagcg gcagctctgg ttctggctct     660

ggttctggcg gtggtggctc tggtggcggt ggctctggtt ctggttacat cccggaagct     720

ccgcgtgacg gtcaggcgta cgttcgtaaa gacggtgaat gggttctgct gtctaccttc     780

ctgggtggag gaggtggctc ctggagccac ccgcagttcg aaaagtaa                   828


<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 12

Gly Gly Gly Gly Ser Gly Gly Gly Gly Ser Gly Gly Gly Gly Ser
1               5                   10                  15


<210> SEQ ID NO 13
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (2)..(6)

<400> SEQUENCE: 13

Ala Glu Ala Ala Ala Lys Ala
1               5


<210> SEQ ID NO 14
<211> LENGTH: 81
<212> TYPE: DNA
<213> ORGANISM: T4 bacteriophage

<400> SEQUENCE: 14

ggttacatcc cggaagctcc gcgtgacggt caggcgtacg ttcgtaaaga cggtgaatgg      60
```

gttctgctgt ctaccttcct g 81

<210> SEQ ID NO 15
<211> LENGTH: 81
<212> TYPE: DNA
<213> ORGANISM: T4 bacteriophage

<400> SEQUENCE: 15
ggttacatcc cggaagctcc gcgtgactgt caggcgtacg ttcgtaaatg cggtgaatgg 60
gttctgctgt ctaccttcct g 81

<210> SEQ ID NO 16
<211> LENGTH: 81
<212> TYPE: DNA
<213> ORGANISM: T4 bacteriophage

<400> SEQUENCE: 16
ggttacatcc cggaagctcc gtgtgacggt caggcgtacg ttcgtaaatg cggtgaatgg 60
gttctgctgt ctaccttcct g 81

<210> SEQ ID NO 17
<211> LENGTH: 81
<212> TYPE: DNA
<213> ORGANISM: T4 bacteriophage

<400> SEQUENCE: 17
ggttacatcc cggaagctcc gtgtgacggt caggcgtacg ttcgtaaaga ctgtgaatgg 60
gttctgctgt ctaccttcct g 81

<210> SEQ ID NO 18
<211> LENGTH: 81
<212> TYPE: DNA
<213> ORGANISM: T4 bacteriophage

<400> SEQUENCE: 18
ggttacatcc cggaagcttg ccgtgacggt caggcgtacg ttcgtaaaga ctgtgaatgg 60
gttctgctgt ctaccttcct g 81

<210> SEQ ID NO 19
<211> LENGTH: 81
<212> TYPE: DNA
<213> ORGANISM: T4 bacteriophage

<400> SEQUENCE: 19
ggttacatcc cggaagctcc gcgtgacggt cagtgctacg ttcgttgcga cggtgaatgg 60
gttctgctgt ctaccttcct g 81

<210> SEQ ID NO 20
<211> LENGTH: 81
<212> TYPE: DNA
<213> ORGANISM: T4 bacteriophage

<400> SEQUENCE: 20
ggttacatcc cggaagctcc gcgtgacggt caggcgtgcg tttgtaaaga cggtgaatgg 60
gttctgctgt ctaccttcct g 81

<210> SEQ ID NO 21
<211> LENGTH: 18
<212> TYPE: PRT

-continued

```
<213> ORGANISM: Artificial sequence
<220> FEATURE:
<223> OTHER INFORMATION: Synthetic polypeptide

<400> SEQUENCE: 21

Gly Ser Gly Ser Gly Ser Gly Gly Gly Gly Ser Gly Gly Gly Gly Ser
1               5                   10                  15

Gly Ser
```